United States Patent [19]

Nogami et al.

[11] Patent Number: 4,877,735

[45] Date of Patent: Oct. 31, 1989

[54] PROCESS FOR PRODUCING 2-KETO-L-GULONIC ACID

[75] Inventors: Ikuo Nogami, Nagaokakyo; Takamasa Yamaguchi, Kobe; Masahide Oka, Kawanishi; Hideo Shirafuji, Nagaokakyo, all of Japan

[73] Assignee: Takeda Chemical Industries, Ltd., Osaka, Japan

[21] Appl. No.: 204,529

[22] Filed: Jun. 8, 1988

[30] Foreign Application Priority Data

Jun. 19, 1987 [JP] Japan .................................. 62-154100

[51] Int. Cl.$^4$ ........................... C12P 7/60; C12P 7/58; C12R 1/01
[52] U.S. Cl. .................................... 435/138; 435/137; 435/822
[58] Field of Search ............... 435/138, 137, 822, 143, 435/147, 148, 190

[56] References Cited

U.S. PATENT DOCUMENTS

| | | | |
|---|---|---|---|
| 2,421,612 | 6/1947 | Gray | 435/138 |
| 3,914,218 | 10/1975 | Celmer et al. | 435/119 |
| 3,963,574 | 6/1976 | Sonoyama et al. | 435/138 |
| 4,013,789 | 3/1977 | Celmer | 435/119 |
| 4,155,812 | 5/1979 | Kita | 435/138 |

FOREIGN PATENT DOCUMENTS 0228273 8/1987 United Kingdom ............... 435/138

*Primary Examiner*—Johnnie R. Brown
*Assistant Examiner*—Pamela S. Webber
*Attorney, Agent, or Firm*—Wenderoth, Lind & Ponack

[57] ABSTRACT

An improved process for producing 2-keto-L-gulonic acid which comprises culturing a microorganism belonging to the genus Pseudogluconobacter which has an ability to oxidize L-sorbose to 2-keto-L-gulonic acid in a culture medium supplemented with a rare earth element in the presence of L-sorbose.

7 Claims, No Drawings

PROCESS FOR PRODUCING 2-KETO-L-GULONIC ACID

FIELD OF THE INVENTION

The present invention relates to a fermentation process for producing 2-keto-L-gulonic acid which is useful as an intermediate for synthesizing L-ascorbic acid.

BACKGROUND OF THE INVENTION

2-Keto-L-gulonic acid which is useful as an intermediate for synthesizing L-ascorbic acid has been produced by the industrially established so-called Reichstein method [see, Helvetica Chimica Acta, 17, 311 (1934)]. However, this method involves many steps and requires a large amount of solvent and, therefore, is insufficient for industrial technology of today.

On the other hand, instead of Reichstein method, several methods mainly employing microorganisms have been proposed. For example, a method which comprises subjecting D-glucose to microbiological oxidation to produce 5-keto-D-gluconic acid, reducing it chemically or microbiologically to obtain L-idonic acid and then oxidizing the resultant microbiologically to obtain 2-keto-L-gulonic acid [see, U.S. Pat. No. 2,421,611]; and a method which comprises oxidizing D-glucose microbiologically to obtain 2,5-diketo-D-gluconic acid, reducing it microbiologically or chemically to obtain 2-keto-L-gulonic acid [see, Japanese Patent Publication Nos. 39-14493, 53-25033, 56-15877 and 59-35920] have been investigated.

However, chemical reduction steps employed in these methods, i.e., the reduction of 5-keto-D-gluconic acid to idonic acid in the former method and the reduction of 2,5-diketo-D-gluconic acid to 2-keto-L-gulonic acid in the latter method are accompanied with problems in stereospecificity and they produce D-gluconic acid and 2-keto-D-gluconic acid as by-products, respectively, which results in decrease in yield. Further, when the above reduction is carried out microbiologically, excessive glucide should be supplied to the microorganisms as a reduction energy source, which also results in lowering of yield. In this respect, when L-sorbose is used as a starting material, 2-keto-L-gulonic acid can be produced only by an oxidation step.

In fact, several trials utilizing this advantage have been made by using bacteria belonging to the genera *Gluconobacter, Pseudomonas, Serratia, Achromobacter* and *Alcaligenes* [see, Biotechnology and Bioengineering, 14, 799 (1972); Japanese Patent Publication No. 41-159 and No. 41160; U.S. Pat. No. 3,043,749; USSR Patent No. 526,660; Japanese Patent Publication No. 49-39838; Acta Microbiological Sinica, 20, 246 (1980) and 21, 185 (1981); Japanese Patent Laid Open Publication No. 62-48389].

However, the disclosed strains give insufficient yield and therefore, they are insufficient for industrial use.

Recently, there has been reported a method for producing 2-keto-L-gulonic acid from D-glucose by using one bacterial strain obtained by introducing 2,5-diketo-D-gluconic acid reductase gene of a microorganism belonging to *Corynebacterium* into a microorganism belonging to *Erwinia* according to DNA recombination technique [see, Science, 230, 144 (1985)]. However, this method is also insufficient for utilizing industrial use from the viewpoint of the amount of 2-keto-L-gulonic acid produced.

OBJECTS OF THE INVENTION

Under these circumstances, the present inventors have studied intensively to obtain an industrially advantageous method for producing 2-keto-L-gulonic acid. As the result, we have already found that bacteria isolated from soil and designated as *Pseudogluconobacter saccharoketogenes* can produce a considerable amount of 2-keto-L-gulonic acid from L-sorbose (see, European Patent Published Application No. 221,707). Then, during the study on the improvement of that method, we have unexpectedly found that the fermentation time is shortened and that the production yield of 2-keto-L-gulonic acid from L-sorbose is remarkably improved by culturing the bacteria in a culture medium supplemented with a rare earth element. It has not been found that a rare earth element can exhibit such a fermentation-promoting effect. We have studied intensively on this phenomenon and, as the result, have attained the present invention.

The main object of the present invention is to provide an improved process for producing 2-keto-L-gulonic acid from L-sorbose.

This object as well as other objects and advantages of the present invention will become apparent to those skilled in the art from the following description.

SUMMARY OF THE INVENTION

According to the present invention, there is provided an improved process for producing 2-keto-L-gulonic acid which comprises culturing a microorganism belonging to the genus *Pseudogluconobacter* which has an ability to oxidize L-sorbose to 2-keto-L-gulonic acid in a culture medium supplemented with a rare earth element in the presence of L-sorbose.

By culturing a microorganism belonging to the genus *Pseudogluconobacter* having an ability to oxidize L-sorbose to 2-keto-L-gulonic acid in the presence of a rare earth element, 2-keto-L-gulonic acid which is an important starting material for synthesis of L-ascorbic acid can be produced efficiently.

DETAILED DESCRIPTION OF THE INVENTION

The microorganism of *Pseudogluconobacter* used in the present invention includes, for example, the following strains described in European Patent Published Application No. 221,707:

*Pseudogluconobacter saccharoketogenes* K591s: FERM BP-1130, IFO 14464;
*Pseudogluconobacter saccharoketogenes* 12-5: FERM BP-1129, IFO 14465;
*Pseudogluconobacter saccharoketogenes* TH14-86: FERM BP-1128, IFO 14466;
*Pseudogluconobacter saccharoketogenes* 12-15: FERM BP-1132, IFO 14482;
*Pseudogluconobacter saccharoketogenes* 12-4: FERM BP-1131, IFO 14483;
*Pseudogluconobacter saccharoketogenes* 22-3: FERM BP-1133, IFO 14484.

Hereinafter, these *Pseudogluconobacter saccharoketogenes* bacteria may be referred to as oxidation bacteria.

The rare earth element used in the present invention includes, for example, scandium (Sc), yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb) and lutetium (Lu). These rare earth elements can be supplemented in the form of metallic powder or slug. Or, they can be used in the form of compounds such as their chlorides, carbonates, sulfates, nitrates, oxides and oxalates. They can be used alone or in combination of two or more rare earth elements, for example, cerium carbonate and lanthanum chloride can be used simultaneously. Further, a crude product obtained during isolation and purification steps of the respective elements can also be used.

The amount of the rare earth element supplemented to the culture medium can be selected from such a range that it does not inhibit growth of the microorganism used. Generally, the effective amount ranges from 0.000001 to 0.1% (W/V), preferably, from 0.0001 to 0.05% (W/V).

As a manner for supplementing the element to the culture medium, it can be previously supplemented to the culture medium, or it can be supplemented intermittently or continuously during culture.

In the process of the present invention, when the starting material, i.e., L-sorbose is added to the culture medium, the total amount thereof can be added to the culture medium at the beginning of culture, or it can be added in several portions or continuously to the liquid culture. The concentration of L-sorbose in the culture medium can be 2 to 40% (W/V), preferably 5 to 30% (W/V) based on the culture medium.

In the culture medium used for culture of the above oxidation bacteria, nutrient sources which can be utilized by the bacterial strains, that is, carbon sources, nitrogen sources, inorganic salts, organic salts and trace nutrients which can be utilized by the strains can be used.

As carbon sources, L-sorbose can be used as it is. In addition, as supplementary carbon sources, for example, glucose, fructose, glycerin, sucrose, lactose, maltose, molasses and the like can be used.

Nitrogen sources include, for example, various kinds of ammonium salts (e.g., ammonium sulfate, ammonium nitrate, ammonium chloride, ammonium phosphate), inorganic or organic compounds containing nitrogen such as corn steep liquor (hereinafter may be referred to as CSL), peptone, meat extract, yeast extract, dried yeast, soybean flour, cottonseed meal, urea and the like.

As inorganic salts, in addition to the above rare earth elements, salts of potassium, sodium, calcium, magnesium, iron, manganese, cobalt, zinc, copper and phosphoric acid can be used.

As trace nutrients needless to say, CoA, pantothenic acid, biotin, thiamine and riboflavin which are essential growth factors of the above bacteria can be added. In addition, flavin mononucleotide (hereinafter may be referred to as FMN) which exhibits promotion activities for growth and production of 2-keto-L-gulonic acid, other vitamins, L-cysteine, L-glutamic acid and sodium thiosulfate and the like, as compounds or native products containing them, can be appropriately added.

These components of the culture medium can be previously added to the culture medium at once. Or, a part or all of them can be added intermittently or continuously to the liquid culture.

As the means for culturing, there can be employed stationary culture, shaking culture or agitating culture or the like. However, for mass production, so-called submerged culture is preferred.

Of course, the culture conditions vary depending on the particular kind of strain, the particular composition of the culture medium and the like and, briefly, they can be selected for each particular case so that the objective product can be produced with the highest efficiency. For example, the culture temperature is preferably 25° to 35° C. and pH of the culture medium is desirably about 5 to 9.

Upon culturing for 10 to 120 hours under the above conditions, 2-keto-L-gulonic acid can be accumulated at the highest concentration. In this case, since pH generally lowers as the objective product accumulates, a suitable basic material, for example, sodium hydroxide, potassium hydroxide or ammonia can be added to always maintain the optimal pH level for microbiological production of 2-keto-L-gulonic acid. Or, a suitable buffer can be added to the culture medium to maintain the optimal pH.

In the present invention, when the microorganism belonging to the genus *Pseudogluconobacter* is cultured in the presence of a rare earth element in a liquid medium containing L-sorbose to produce and accumulate 2-keto-L-gulonic acid in the culture medium, the amount of accumulated 2-keto-L-gulonic acid can be remarkably increased by mixing the above oxidation bacteria with another microorganism in comparison with using the oxidation bacteria, i.e., the microorganisms belonging to *Pseudogluconobacter* alone.

The microorganisms to be mixed include, for example, bacteria belonging to the genera *Bacillus, Pseudomonas, Proteus, Citrobacter, Enterobacter, Erwinia, Xanthomonas, Flavobacterium, Micrococcus, Escherichia* and the like. More particularly, the following bacteria are included:

*Bacillus cereus* IFO 3131;
*Bacillus licheniformis* IFO 12201;
*Bacillus megaterium* IFO 12108;
*Bacillus pumilus* IFO 12090;
*Bacillus amyloliquefaciens* IFO 3022;
*Bacillus subtilis* IFO 13719;
*Bacillus circulans* IFO 3967;
*Pseudomonas trifolii* IFO 12056;
*Pseudomonas maltophilia* IFO 12692;
*Proteus inconstans* IFO 12930;
*Citrobacter freundii* IFO 13544;
*Enterobacter cloacae* IFO 3320;
*Erwinia herbicola* IFO 12686;
*Xanthomonas pisi* IFO 13556;
*Xanthomonas citri* IFO 3835;
*Flavobacterium meningosepticum* IFO 12535;
*Micrococcus varians* IFO 3765;
*Escherichia coli* IFO 3366.

A liquid culture obtained by culturing any of these bacteria in a suitable medium at 20 to 40° C. for 1 to 4 days can be used as a seed culture of the microorganism to be mixed. In general, the amount to be inoculated is desirably 1/10 to 1/1000 of that of the oxidation bacteria (*Pseudogluconobacter*). When mixed culture is carried out by mixing the microorganism to be mixed with the oxidation bacteria in such an amount to be inoculated, the growth of the oxidation bacteria can be promoted and thereby L-sorbose a higher concentration can be oxidized to 2-keto-L-gulonic acid within a shorter period of time in comparison with culture using the oxidation bacteria alone. The bacteria to be used as the microorganism to be mixed desirably have no or weak assimilation property with L-sorbose which is the starting material of the present invention, or 2-keto-L-gulonic acid which is the objective product of the present invention. Other culture conditions are the same as those using the oxidation bacteria alone. In addition, the sterilized culture of certain kinds of bacteria other than the above oxidation bacteria can be effectively utilized as an ingredient of the culture medium. Bacteria which can be utilized include, for example, those of the genera *Bacillus, Pseudomonas, Citrobacter, Escherichia* and *Erwinia*. More particularly, the following bacteria are included:

*Bacillus cereus* IFO 3131;
*Bacillus subtilis* IFO 3023;
*Bacillus pumilus* IFO 12089;
*Bacillus megaterium* IFO 12108;
*Bacillus amyloliquefaciens* IFO 3022;
*Pseudomonas trifolii* IFO 2056;
*Citrobacter freundii* IFO 12681;
*Escherichia coli* IFO 3546;
*Erwinia herbicola* IFO 12686.

These bacteria can be cultured in a medium in which they can grow at 20 to 40° C. for 2 to 4 days. The resultant culture can be sterilized and added to the culture medium of the present oxidation bacteria in an amount of 0.5 to 5.0% (V/V) to promote the growth of the oxidation bacteria.

2-Keto-L-gulonic acid thus produced and accumulated in the culture medium can be isolated and purified by known means utilizing its properties.

2-Keto-L-gulonic acid can be isolated as a free acid. Or, it can be isolated, for example, as a salt with sodium, potassium, calcium or ammonium.

As a method for isolation, there can be employed, for example, a method wherein bacterial cells are removed from the culture medium by filtration or centrifugation as needed, subsequently, the solution is concentrated without or after treatment with activated carbon, and separated crystals are collected by filtration and recrystallized to obtain the objective product; solvent extraction; chromatography; salting out and the like. These methods can be employed alone, in appropriate combination thereof, or in repetition.

When 2-keto-L-gulonic acid is obtained in the free form, it can be converted into, for example, a salt of sodium, potassium, calcium, ammonium or the like and, when it is obtained as a salt, it can be converted into the free form or other salts by an appropriate method.

2-Keto-L-gulonic acid produced in the culture medium was determined by high performance liquid chromatography under the following conditions.

The conditions of measurement of high performance liquid chromatography:
HPLC: 655A system (manufactured by Hitachi Seisakusho, Japan)
Column: SCR 101H (sulfonated polystyrene gel), 300×7.9 mm (manufactured by Simadzu Seisakusho, Japan)
Flow rate: 0.8 ml/min. (pressure: 50 kg/cm$^2$)
Mobile phase: diluted sulfuric acid (pH 2.1)
Detector: UV (214 nm) and differential refractometer.
Retention time: 7.20 min. for 2-keto-L-gulonic acid and 8.33 min. for L-sorbose.

The following examples further illustrate the present invention in detail but are not to be construed to limit the scope thereof. All percentages used for the culture media are % (W/V) unless otherwise described. The yields for the cultures in the examples are expressed by mole conversion yield of the amount of 2-keto-L-gulonic acid produced based on that of L-sorbose used.

Example 1

TABLE 1

| Slant Medium (g/l) | |
|---|---|
| D-Sorbitol | 25 |
| Peptone | 10 |
| Yeast Extract | 10 |
| CaCO$_3$ | 2 |
| Agar | 20 |
| | pH 7.0 |

A seed culture medium (20 ml) composed of D-glucose 2.0%, peptone 1.0%, dried yeast 1.0% and CaCO$_3$ (Akadama, produced by Shiraishi Calcium Kaisha Ltd., Japan) 2.0% was distributed in a 200 ml Erlenmeyer flask and autoclaved at 120° C. for 20 minutes. This flask was inoculated with one loopful of *Pseudogluconobacter saccharoketogenes* K591s strain (IFO 14464, FERM BP-1130) which had been grown on the slant medium as shown in Table 1 at 30° C. for 3 days, and cultured with shaking (200 rpm) at 30° C. for 2 days. The resulting culture (2 ml) was transferred to the same medium as described above and cultured under the same conditions to give a second seed culture.

A fermentation medium (25 ml) composed of CSL 2.0%, dried yeast 0.5%, ammonium sulfate 0.3%, Na$_2$S$_2$O$_3$.5H$_2$O 0.05%, FeSO$_4$.7H$_2$O 0.1%, CeCl$_3$.7H$_2$O 0.005%, CaCO$_3$ (Akadama) 3.5%, and L-sorbose, 9.5% (separately sterilized) was distributed in a 200 ml Erlenmeyer flask and autoclaved at 120° C. for 20 minutes.

This was inoculated with the above second seed culture (1.25 ml) and cultured with shaking at 30° C. for 2 days. The fermentation solution thus obtained contained 86.4 mg/ml of 2-keto-L-gulonic acid (yield: 84.4%) according to the determination by nigh performance liquid chromatography. A fermentation solution obtained by culturing according to the same manner except that no cerium chloride was supplemented to the medium contained 51.0 mg/ml of 2-keto-L-gulonic acid (yield: 49.8%).

Example 2

*Pseudogluconobacter saccharoketogenes* 12-4 (IFO 14483, FERM BP-1131), 12-5 (IFO 14465, FERM BP-1129), 12-15 (IFO 14482, FERM BP-1132) and 22-3 (IFO 14484, FERM BP-1133) strains were cultured according to the same manner as described in Example 1 to obtain second seed cultures.

A fermentation medium (25 ml) composed of CSL 2.0%, dried yeast 0.5%, ammonium sulfate 0.3%, Na$_2$S$_2$O$_3$.5H$_2$O 0.05%, FeSO$_4$.7H$_2$O 0.01%, Ce$_2$(CO$_3$)$_3$.8H$_2$O 0.05%, CaCo$_3$ (Akadama) 3.5% and L-sorbose 9.5% (separately sterilized) was distributed in a 200 ml Erlenmeyer flask and autoclaved at 120° C. for 20 minutes.

Each of the above second seed cultures (1.25 ml) was transferred in the Erlenmeyer flask containing the fermentation medium and cultured with shaking at 30° C. for 3 days. The fermentation solution thus obtained was determined by high performance liquid chromatography. The results are shown in Table 2 as the amount of 2-keto-L-gulonic acid produced (mg/ml) together with those obtained by culturing on a medium in which no Ce$_2$(CO$_3$)$_3$.8H$_2$O was added.

TABLE 2

| Strains | Cerium Carbonate | |
| --- | --- | --- |
| | Not added | Added |
| 12-4 | 51.0 (49.8%) | 63.0 (61.5%) |
| 12-5 | 75.9 (74.1%) | 87.6 (85.6%) |
| 22-15 | 45.2 (44.1%) | 67.3 (65.7%) |
| 22-3 | 69.8 (68.1%) | 88.1 (86.1%) |

The data in the parentheses mean yield.

EXAMPLE 3

*Pseudogluconobacter saccharoketogenes* TH14-86 (IFO 14466, FERM BP-1128) was cultured according to the same manner as described in Example 1 to give a second seed culture.

A fermentation medium (25 ml) composed of CSL 2.0%, dried yeast 0.5%, ammonium sulfate 0.3%, $Na_2S_2O_3.5H_2O$ 0.05%, $FeSO_4.7H_2O$ 0.1%, $CaCO_3$ (Akadama) 5% and L-sorbose 10.5% (separately sterilized) was distributed in a 200 ml Erlenmeyer flask and autoclaved at 120° C. for 20 minutes. The above second seed culture (1.25 ml) was transferred in the Erlenmeyer flask containing the fermentation medium and cultured with shaking at 30° C. for 2 days. Under these conditions, shaking culture was carried out by supplementing 0.01% of a chloride of yttrium, lanthanum, cerium, neodymium, samarium, europium, gadolinium, terbium, dysprosium, holmium, erbium or ytterbium, or praseodymium oxide, or 0.05% of scandium oxide at 30° C. for 2 days. The fermentation solution thus obtained was determined by high performance liquid chromatography. The amount of 2-keto-L-gulonic acid produced in the culture medium (mg/ml) is shown in Table 3.

TABLE 3

| Rare earth element | Amount of produced 2-keto-L-gulonic acid |
| --- | --- |
| Not added | 78.5 (69.4%) |
| $YCl_3.6H_2O$ | 86.9 (76.8%) |
| $LaCl_3.7H_2O$ | 97.6 (86.3%) |
| $CeCl_3.7H_2O$ | 97.6 (86.3%) |
| $NdCl_3.6H_2O$ | 90.1 (79.6%) |
| $SmCl_3.6H_2O$ | 84.1 (74.3%) |
| $EuCl_3.6H_2O$ | 83.0 (73.4%) |
| $GdCl_3.6H_2O$ | 81.9 (72.4%) |
| $TbCl_3.xH_2O$ | 82.0 (72.5%) |
| $DyCl_3.6H_2O$ | 82.1 (72.6%) |
| $HoCl_3.6H_2O$ | 81.9 (72.4%) |
| $ErCl_3.6H_2O$ | 82.2 (72.6%) |
| $YbCl_3.6H_2O$ | 82.2 (72.6%) |
| $Pr_6O_{11}$ | 94.6 (83.6%) |
| $Sc_2O_3$ | 80.6 (71.2%) |

The data in the parentheses mean yield.

EXAMPLE 4

According to the same manner as described in Example 1, *Pseudogluconobacter saccharoketogenes* TH 14-86 strain was cultured by using the same fermentation medium as described in Example 1 to which lanthanum oxide, chloride, carbonate, nitrate or oxalate, or cerium oxide, chloride, sulfate or carbonate in the amount shown in Table 4 was added. In this case, the culture period was 30 hours. The amount of 2-keto-L-gulonic acid (mg/ml) produced in the fermentation solution obtained was determined by high performance liquid chromatography. The results are shown in Table 4 together with those obtained by culture without supplement of the rare earth element.

TABLE 4

| Rare earth element | Amount added (%) | Amount of produced 2-keto-L-gulonic acid |
| --- | --- | --- |
| Not added | 0 | 60.8 (59.4%) |
| $LaCl_3.7H_2O$ | 0.002 | 74.3 (72.6%) |
| $La_2(CO_3)_3$ | 0.002 | 74.0 (72.3%) |
| $La(NO_3)_3.6H_2O$ | 0.002 | 73.6 (71.9%) |
| $La_2(C_2O_4)_3.9H_2O$ | 0.002 | 73.1 (71.4%) |
| $La_2O_3$ | 0.05 | 74.5 (72.8%) |
| $CeCl_3.7H_2O$ | 0.002 | 73.1 (71.4%) |
| $Ce_2(CO_3)_3.8H_2O$ | 0.002 | 73.8 (72.1%) |
| $Ce_2(CO_3)_3.nH_2O$ | 0.002 | 73.2 (71.5%) |
| $CE(SO_4)_2.nH_2O$ | 0.002 | 75.1 (73.4%) |
| $CeO_2$ | 0.05 | 64.5 (63.0%) |

The data in the parentheses mean yield.

EXAMPLE 5

Microbial cells of *Bacillus megaterium* (IFO 12108) grown on the slant medium shown in Table 1 at 28° C. for 2 days were suspended in 10 ml of sterilized water, and all of them were transferred in a Sakagucni flask containing seed culture medium (500 ml) of Example 1 and cultured with reciprocal shaking (85 spm) at 28° C. for 2 days to give a seed culture of *Bacillus megaterium*. A medium (30 liter, pH 7.0) composed of sucrose 4.0%, cottonseed meal 4.0%, $K_2HPO_4$ 0.65%, $KH_2PO_4$ 0.55%, ammonium sulfate 0.05%, NaCl 0.05%, $MgSO_4.7H_2O$ 0.05% and calcium patothenic acid 0.05% was charged in a 50 liter fermentor and autoclaved at 125° C. for 20 minutes. The fermentor was inoculated with the seed culture of *Bacillus megaterium* (1 liter) and cultured for 4 days under the following conditions: agitation 200 rpm, aeration 24 liters/min., inner pressure 1.0 kg/cm$^2$ and temperature 28° C. The resulting culture was autoclaved at 120° C. for 20 minutes, stored at a cold place and the sterilized culture of *Bacillus megaterium* (hereinafter referred to as mega broth) was used as one of the components of the fermentation medium.

The seed culture medium of Example 1 (20 ml) was distributed in a 200 ml Erlenmeyer flask and autoclaved at 120° C. for 20 minutes. One loopful of microbial cells of *Pseudogluconobacter saccharoketogenes* TH14-86 strain grown on the slant medium shown in Table 1 at 28° C. for 4 days were inoculated in the above flask and cultured with shaking at 30° C. for 2 days. The culture obtained (20 ml) was placed in a 1 liter Erlenmeyer flask containing a culture medium (200 ml) composed of D-glucose 2.0%, mega broth 3.0% (V/V), CSL 1.0%, yeast extract 0.5%, peptone 0.1%, ammonium sulfate 0.3% and $CaCO_3$ (Akadama) 2.0% and cultured with shaking at 30° C. for 2 days to give a second seed culture of TH14-86 strain.

Separately, a 200 ml Erlenmeyer flask containing the seed culture medium of Example 2 (20 ml) was inoculated with one loopful of microbial cells of *Bacillus megaterium* IFO 12108 grown on a slant medium at 28° C. for 2 days, and subjected to shaking culture at 28° C. for 2 days to give a seed culture of the microorganism to be mixed.

L-Sorbose (72 g) was dissolved in water to make up the volume to 300 ml. Then, CSL (60 g), dried yeast (6 g), ammonium sulfate (9 g), $FeSO_4.7H_2O$ (3 g), FMN (3 mg), thiamine (3 mg), biotin (1.5 mg) and actcol (produced by Takeda Chemical Industries, Ltd., Japan) (0.5 g) were dissolved or suspended in water to make up the volume to 800 ml. Separately, $CaCO_3$ (Akadama, 240 g)

and Ce$_2$(CO$_3$)$_3$.8H$_2$O (150 mg) were suspended in water to 1,000 ml. After autoclaving each medium at 120° C. for 20 minutes, they were charged in a 5 liter fermentor which had been previously sterilized.

The second seed culture of the above TH14-86 strain (300 ml) and the seed culture of the microorganism to be mixed (4 ml) were inoculated in this fermentor and culture was started under the following conditions: temperature 30° C., aeration 2.4 liter/min. and agitation 800 rpm.

Separately, L-sorbose (528 g) and LaCl$_3$.7H$_2$O (150 mg) were dissolved in water to make up the volume to 900 ml. Ammonium sulfate (6 g) and FeSO$_4$.7H$_2$O (3 g) were dissolved in water to make up the volume to 100 ml. These were autoclaved at 120° C. for 20 minutes, respectively, and then aseptically mixed. From the 6th hour after initiation of culture, this mixture was continuously added to the fermentor and addition was completed in 24 hours. After addition of the mixture was completed, culture was further carried out for 8 hours (total culture period: 38 hours), thereby, L-sorbose in the culture was completely consumed and 3.16 liters of a fermentation solution was obtained. The fermentation solution contained 176.0 mg/ml of 2-keto-L-gulonic acid (yield: 86.0 %).

Separately, culture was carried out under the same conditions as described above except that Ce$_2$(CO$_3$)$_3$.8H$_2$O and LaCl$_3$.7H$_2$O were not supplemented. In this case, when culture was further carried out for 22 hours after supplement of the mixture, L-sorbose was completely consumed (total culture period: 52 hours).

161.4 mg/ml of 2-keto-L-gulonic acid was produced in the fermentation solution thus obtained (3.09 liters) (yield: 77.1%).

EXAMPLE 6

About 260 ml of 6N sulfuric acid was added with stirring to the fermentation solution obtained in Example 5 containing 176.0 mg/ml of 2-keto-L-gulonic acid (1 liter) and insolubles formed such as plaster and cells, were removed by centrifugation. The resulting supernatant (1,150 ml) was passed through a column packed with cation exchange resin IR 120B (H$^+$ type, produced by Rohm and Haas, U.S.A.) (200 ml) and the column was washed with distilled water (150 ml). The eluate and washings were combined and passed through a column packed with Shirasagi carbon for chromatography (produced by Takeda Chemical Industries Ltd., Japan) (200 ml) and the column was washed with distilled water (150 ml). The combined solution of the eluate and washings (1,450 ml) was concentrated to 250 ml under reduced pressure at about 50° C. The concentrate was allowed to stand at 5° C. overnight to separate 2-keto-L-gulonic acid. The crystals obtained were collected by filtration and washed with small amount of chilled water, 50% cold methanol and cold methanol. The resultant was dried over phosphorus pentoxide under reduced pressure to give 156 g of 2-keto-L-gulonic acid monohydrate as colorless crystals (yield: 81.1%).

Melting point: 171° C. (decomp.)

Elemental analysis (%): for C$_6$H$_{10}$O$_7$.H$_2$O: Calcd: C, 33.97; H, 5.62. Found: C, 33.91; H, 5.65.

Specific rotation: $[\alpha]_D^{18} = -48°$ (c=1.0 in H$_2$O).

EXAMPLE 7

One loopful of microbial cells of *Pseudogluconobacter saccharoketogenes* TH14-86 strain was inoculated in a 200 ml Erlenmeyer flask containing a medium (20 ml) composed of D-glucose 2.0%, mega broth 3.0% (V/V), CSL 1.0%, yeast extract 0.5%, peptone 0.1%, ammonium sulfate 0.3% and CaCO$_3$(Super #1700 produced by Maruo Calcium K.K., Japan) 2.0% and subjected to shaking culture at 30° C. for 2 days. The culture obtained (2 ml) was transferred to a 200 ml Erlenmeyer flask containing the same medium (20 ml) and, according to the same manner, culture was carried out to give a second seed culture of the oxidation bacterium.

The fermentation medium (25 ml) composed of CSL 2.0%, dried yeast 0.5%, ammonium sulfate 0.3%, Na$_2$S$_2$O$_3$.5H$_2$O 0.05%, FeSO$_4$.7H$_2$O 0.1%, CaCO$_3$ (Super #1700, produced by Maruo Calcium K.K., Japan) 5% and L-sorbose 12.5% (separately sterilized) was distributed in a 200 ml Erlenmeyer flask and autoclaved at 120° C. for 20 minutes. The separately sterilized CeCl$_3$.7H$_2$O in the amount shown in Table 5 was added to the Erlenmeyer flask containing this fermentation medium and the flask was inoculated with the above-described second seed culture (1.25 ml) and seed culture (0.1 ml) of the microorganism to be mixed obtained in Example 5.

The amount of 2-keto-L-gulonic acid (mg/ml) in the fermentation solution obtained by shaking culture at 30° C. for 3 days is shown in Table 5.

TABLE 5

| Added amount of CeCl$_3$.7H$_2$O (%) | Produced amount of 2-keto-L-gulonic acid |
|---|---|
| 0 | 105.3 (78.2%) |
| 0.002 | 116.3 (86.3%) |
| 0.01 | 119.7 (88.9%) |
| 0.05 | 118.2 (87.8%) |

* The data in the parentheses mean yield.

EXAMPLE 8

A second seed culture of the oxidation bacterium TH14-86 strain was obtained by culture according to the same manner as described in Example 7. The fermentation medium (25 ml) composed of CSL 2.0%, dried yeast 0.5%, ammonium sulfate 0.3%, Na$_2$S$_2$O$_3$.5H$_2$O 0.05%, FeSO$_4$.7H$_2$O 0.1%, CaCO$_3$ (guaranteed reagent produced by Wako Pure Chemical Industries, Japan) 2.5% and L-sorbose 7.5% (separately sterilized) was distributed and sterilized in a 200 ml Erlenmeyer flask. The separately sterilized CeCl$_3$.7H$_2$O in the amount shown in Table 6 was supplemented in the Erlenmeyer flask containing this fermentation medium and inoculated with the above second seed culture (1.25 ml). The amount of 2-keto-L-gulonic acid (mg/ml) in the fermentation solution obtained by shaking culture at 30° C. for 3 days is shown in Table 6.

TABLE 6

| Added amount of CeCl$_2$.7H$_2$O (%) | Produced amount of 2-keto-L-gulonic acid |
|---|---|
| 0 | 30.0 (37.1%) |
| 0.00001 | 61.2 (75.7%) |
| 0.0001 | 67.1 (83.0%) |
| 0.001 | 70.7 (87.5%) |
| 0.01 | 70.6 (87.4%) |
| 0.1 | 70.5 (87.2%) |

The data in the parentheses mean yield.

EXAMPLE 9

A second seed culture of the oxidation bacterium. TH-14-86 strain was obtained by culture according to the same manner as described in Example 7. The fermentation medium (20 ml) composed of CSL 2.0%, dried yeast 0.5%, ammonium sulfate 0.3%, $Na_2S_2O_3.5H_2O$ 0.05%, $FeSO_4.7H_2O$, 0.1%, $CaCO_3$ (Super #1700) 5.0%, L-sorbose 12.0% (separately sterilized) and additives shown in Table 7 in the shown amount were distributed and sterilized in a 200 ml Erlenmeyer flask. The flask was inoculated with the above second seed culture (1 ml) and subjected to shaking culture at 30° C. for 2 days. The amount of the produced 2-keto-L-gulonic acid (mg/ml) in the obtained culture was determined by high performance liquid chromatography. The results are shown in Table 7 together with those obtained by culture without addition.

TABLE 7

| Additives | Amount added (%) | Amount of produced of 2-keto-L-gulonic acid |
|---|---|---|
| Nothing | 0 | 85.1 (65.8%) |
| $LaCl_3.7H_2O$ | 0.005 | 105.4 (81.5%) |
| $NdCl_3.6H_2O$ | 0.005 | 105.4 (81.5%) |
| $CeCl_3.7H_2O$ | 0.005 | 105.8 (81.8%) |
| $NdCl_3.6H_2O$ | 0.005 | 105.8 (81.8%) |
| $HoCl_3.6H_2O$ | 0.005 | 105.8 (81.8%) |
| Lanthanum[1] (lump) | 0.005 | 102.9 (79.6%) |
| Neodymium[2] (metal) | 0.005 | 99.4 (79.6%) |
| Crude rare earth Chloride[3] | 0.005 | 103.6 (80.1%) |
| Mixed rare earth Oxide[4] | 0.005 | 101.9 (78.8%) |

Note:
[1] and [2] manufactured by Wako Pure Chemical Industries, Japan.
[3] Crude, rare earth chloride (manufactured by Mitsubishi Chemical Industries Ltd., Japan containing rare earth elements Ce (18.3%), La (10.0%), Nd (7.1%) and Pr (2.0%).)
[4] Mixed rare earth oxide (manufactured by Santoku Metal Industry Co., Ltd., Japan, the composition being $La_2O_3$ 29.5%, $CeO_2$ 50.0%, $Pr_6O_{11}$ 4.9%, $Nd_2O_3$ 16.0% and $Sm_2O_3$ not more than 0.03%).

The data in the parentheses mean yield.

What is claimed is:

1. A process for producing 2-keto-L-gulonic acid which comprises culturing a microorganism belonging to the genus *Pseudogluconobacter* which has an ability to oxidize L-sorbose to 2-keto-L-gulonic acid in a culture medium supplemented with a rare earth element in the presence of L-sorbose.

2. A process according to claim 1, wherein the rare earth element is a member selected from the group consisting of scandium, yttrium, lanthanum, cerium, praseodymium, neodymium, samarium, europium, gadolinium, terbium, dysprosium, holmium, erbium, thulium, ytterbium and lutetium.

3. A process according to claim 1, wherein one or a plurality of the rare earth elements are supplemented in the form of metallic powder, metallic slug, chlorides, carbonates, sulfates, nitrates, oxides and oxalates.

4. A process according to claim 1, wherein the rare earth element is supplemented in an amount of 0.000001 to 0.1% (W/V) based on the medium.

5. A process according to claim 4, wherein the amount is 0.0001 to 0.05% (W/V).

6. A process according to claim 1, wherein the microorganism is *Pseudogluconobacter saccharoketogenes*.

7. A process according to claim 6, wherein the microorganism is *Pseudogluconobacter saccharoketogenes* K591s (FERM BP-1130), 12-5 (FERM BP-1129), TH14-86 (FERM BP-1128), 12-15 (FERM BP-1132), 12-4 (FERM BP-1131) or 22-3 (FERM BP-1133).

* * * * *